US008971991B2

(12) United States Patent
Watson

(10) Patent No.: US 8,971,991 B2
(45) Date of Patent: Mar. 3, 2015

(54) SUPPLEMENTAL TRANSMISSION INFORMATION FOR ATTENUATION CORRECTION IN POSITRON EMISSION TOMOGRAPHY IMAGING

(71) Applicant: Charles C. Watson, Knoxville, TN (US)

(72) Inventor: Charles C. Watson, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 229 days.

(21) Appl. No.: 13/763,948

(22) Filed: Feb. 11, 2013

(65) Prior Publication Data

US 2014/0228673 A1 Aug. 14, 2014

(51) Int. Cl.
| A61B 5/05 | (2006.01) |
| A61B 6/00 | (2006.01) |
| A61B 5/00 | (2006.01) |
| A61B 5/055 | (2006.01) |
| A61B 6/03 | (2006.01) |

(52) U.S. Cl.
CPC ............. *A61B 6/5247* (2013.01); *A61B 5/0035* (2013.01); *A61B 5/055* (2013.01); *A61B 5/742* (2013.01); *A61B 6/037* (2013.01); *A61B 6/4417* (2013.01); *A61B 6/461* (2013.01); *A61B 6/5258* (2013.01); *A61B 6/582* (2013.01)
USPC ........................................................ 600/411

(58) Field of Classification Search
CPC .... A61B 6/5247; A61B 6/037; A61B 6/4417; A61B 6/461; A61B 5/0035; A61B 5/055; A61B 5/742
USPC ........................................................ 600/411
See application file for complete search history.

(56) References Cited

U.S. PATENT DOCUMENTS

| 6,410,919 | B1 | 6/2002 | Nickles | |
| 2005/0096532 | A1* | 5/2005 | Block et al. | 600/411 |
| 2007/0106154 | A1* | 5/2007 | Conti | 600/436 |
| 2008/0139924 | A1* | 6/2008 | Eberler et al. | 600/411 |
| 2008/0208035 | A1* | 8/2008 | Nistler et al. | 600/411 |
| 2010/0331665 | A1* | 12/2010 | Ladebeck | 600/411 |

OTHER PUBLICATIONS

R. J. Nickles, "A Positron Floodlight for PET Attenuation Measurements," IEEE Transactions on Nuclear Science, vol. 48, No. 1, pp. 157-161, Feb. 2001.
C. Watson et al., "Applications of Positron Beams in an Integrated MR/PET," Brochure, Siemens Healthcare, pp. 1-19, May 2012.
J. Nuyts et al., "Completion of a Truncated Attenuation Image from the Attenuated PET Emission Date," IEEE, pp. 1-10, 2011.
(Continued)

*Primary Examiner* — Long V Le
*Assistant Examiner* — Bo J Peng
(74) *Attorney, Agent, or Firm* — Peter Kendall

(57) ABSTRACT

Supplemental transmission information is used in PET imaging with a hybrid PET/MR system. The magnetic field of the MR portion is used to direct positrons from one or more sources outside or inside the PET field of view to within the PET field of view. An oblique target or targets create an annihilation source within the PET field of view from the positron beam or beams. The resulting radiation may be detected. In combination with measurements made with the sources shielded (e.g., no positron beam-target annihilation sources), the attenuation or other characteristics outside the uniform region of the MR field of view is determined, such as calculating attenuation of arms of a patient for attenuation correction in PET imaging.

17 Claims, 5 Drawing Sheets

(56) References Cited

OTHER PUBLICATIONS

J. Nuyts et al., "Simultaneous Maximum A Posteriori Reconstruction of Attenuation and Activity Distributions from Emission Sinograms," IEEE Transactions of Medical Imaging, vol. 18, No. 5, pp. 393-403, May 1999.

C. Watson et al., "Physics and applications of positron beams in an integrated PET/MR," Phys. Med. Biol., 58, 1.1-1.12, 2013.

* cited by examiner

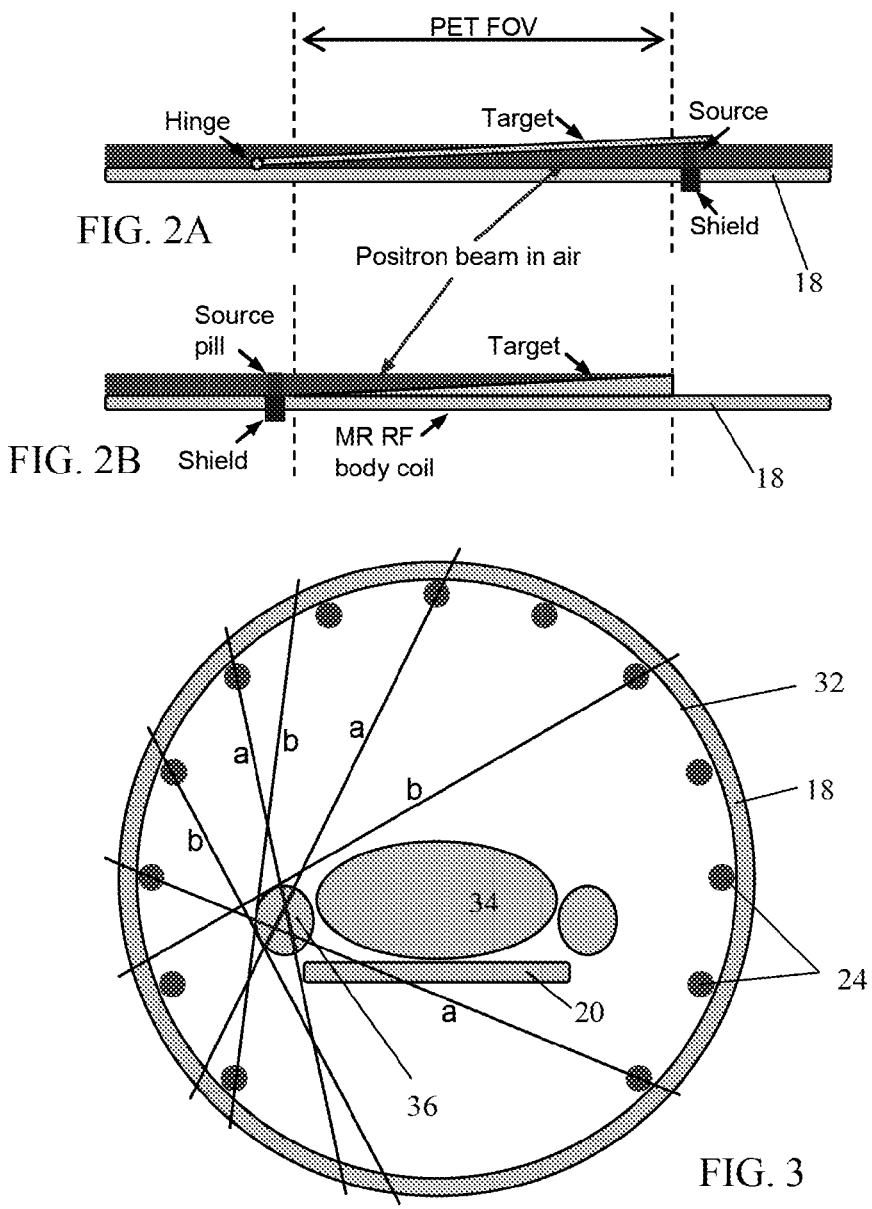

FIG. 5A
FIG. 5B
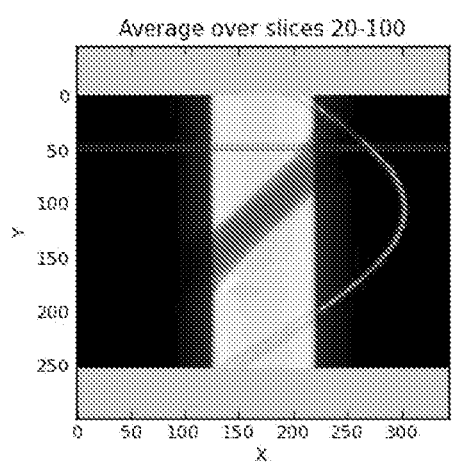
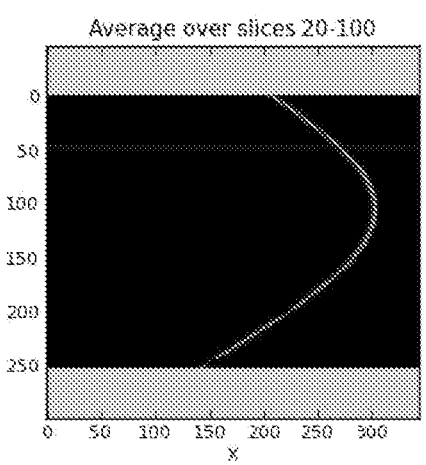
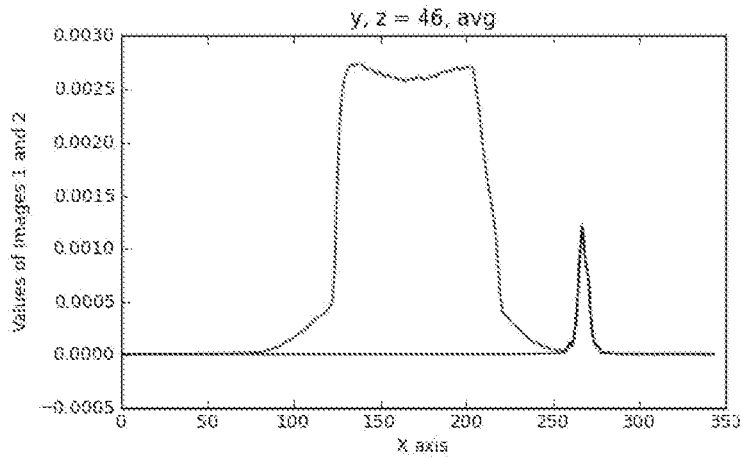
FIG. 5C

FIG. 6A
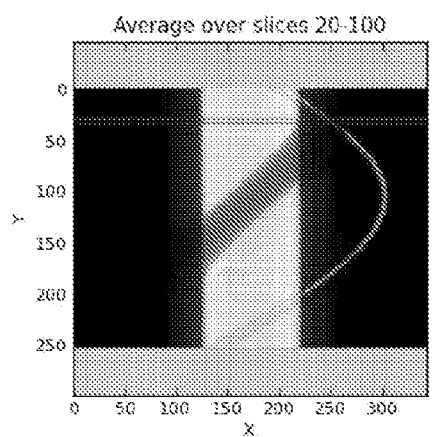
FIG. 6B
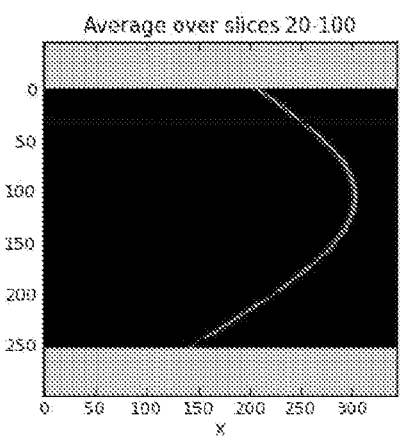
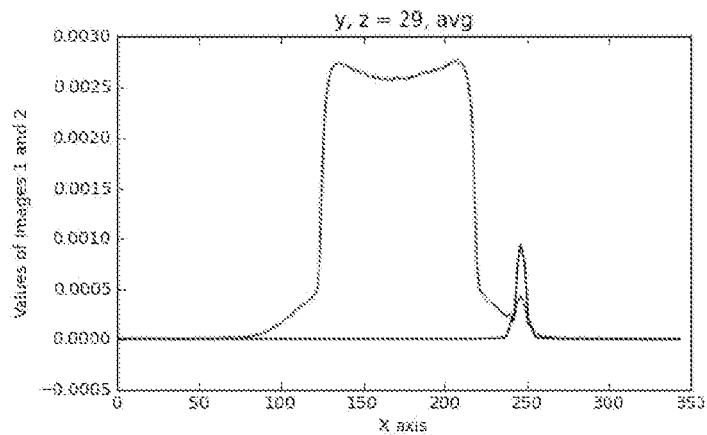
FIG. 6C

SUPPLEMENTAL TRANSMISSION INFORMATION FOR ATTENUATION CORRECTION IN POSITRON EMISSION TOMOGRAPHY IMAGING

BACKGROUND

The present embodiments relate to positron emission tomography (PET). In particular, supplemental transmission information is used in PET for attenuation correction.

PET imaging may be combined with another imaging modality in a hybrid system. One example is a combination of PET with magnetic resonance (MR). The axial fields of view (FOV) of the individual modalities are as close together as possible in order to minimize the impact of patient motion and increase correlation of the respective data sets. In order for the MR and PET fields of view to overlap, the PET detectors are placed within the MR's axial field of view, as an insert between the MR gradient and radio-frequency body coils.

A hybrid PET/MR system provides benefits for PET imaging. The MR portion may be used to assist in the attenuation correction of PET imaging data. However, MR-based human attenuation correction for PET on integrated PET/MR systems remains problematic. The undistorted MR transaxial field of view at about 45 cm is smaller than the PET transaxial FOV and tunnel diameter, 60 cm. The magnetic field for MR may have spatial distortions or not be uniform outside of the 45 cm radius. This leads to truncation of the patient's body, particularly the arms. Arm truncation causes serious quantitative errors in both attenuation correction and scatter correction of the PET data. In addition, the process of converting an MR image to PET attenuation correction coefficients involves segmenting the MR image into different tissue classes and then assigning assumed linear attenuation coefficient values to these tissues. However, the MR signal frequently does not differentiate clearly between certain tissue types, such as bone and lung tissue, that have very different PET attenuation characteristics. This can result in distortions and inaccuracies in the MR-derived image of PET linear attenuation coefficients, even within the MR FOV.

In one approach, a maximum likelihood for attenuation and activity (MLAA) algorithm uses the PET emission data itself to provide an estimate of a linear attenuation coefficient (LAC) image in the truncated region. However, the shapes and LAC values of the MLAA-estimated arms may be inaccurate, and MLAA may even fail entirely when there is minimal non-specific uptake in the body and arms.

BRIEF SUMMARY

By way of introduction, the preferred embodiments described below include methods, systems, and non-transitory computer readable media with instructions for using supplemental transmission information in PET imaging with a hybrid PET/MR system. The magnetic field of the MR portion is used to direct positrons from one or more sources outside the PET FOV to within the PET FOV by causing the positrons to form beams. One or more targets placed within the FOV create positron annihilation sources where the targets intersect the positron beams. The resulting radiation may be detected. In combination with measurements made with the sources shielded (e.g., no positron beam-target annihilation sources), the attenuation or other characteristics outside the uniform region of the MR field of view is determined, such as calculating attenuation of arms of a patient for attenuation correction in PET imaging.

In a first aspect, a method for attenuation correction for positron emission tomography (PET) in a combined PET and magnetic resonance (MR) imaging system is provided. A positron source in a magnetic field generates a positron beam in a field of view of PET detectors of the combined PET and MR system. The positron beam intersects a target within the field of view of the PET detectors. The PET detectors detect gamma radiation resulting from the intersection of the positron beam with the target. Attenuation correction factors are determined as a function of the detected gamma radiation.

In a second aspect, a hybrid magnetic resonance (MR) and positron emission tomography (PET) system is provided. A MR magnet for generating a magnetic field in a bore and PET detectors within the magnetic field are provided. A plurality of positron sources is spaced apart within the magnetic field and outside a field of view of the PET detectors. A plurality of targets is positionable normally or obliquely to positron beams generated by the positron sources in the magnetic field.

In a third aspect, a method is provided for determining a characteristic of tissues or other materials for positron emission tomography (PET) in a region where the MR image is distorted, truncated or otherwise inaccurately represents attenuating tissues or materials within the PET FOV. A transmission line source is produced within a PET field of view in the region of the distorted, truncated, or inaccurate MR image with a positron beam guided by the magnetic field. The characteristic of the tissue in the region is determined as a function of emissions generated by the transmission line source.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIGS. 2A and 2B illustrate example arrangements for an annihilation source in a hybrid PET/MR system;

FIG. 3 shows an example arrangement of annihilation sources in a bore of a hybrid PET/MR system;

FIG. 5A shows a sinogram of structure in an arm position with radiation from a transmission source, FIG. 5B shows a sinogram of a blank scan with the transmission source, and FIG. 5C shows example profiles through the transmission and blank sinograms outside the arm position; and FIG. 6A shows a sinogram of structure in an arm position with radiation from a transmission source, FIG. 6B shows a sinogram of a blank scan with the transmission source, and FIG. 6C shows example profiles through the transmission and blank sinograms inside the arm position.

DETAILED DESCRIPTION OF THE DRAWINGS AND PRESENTLY PREFERRED EMBODIMENTS

A hybrid PET/MR system is provided for whole body or other imaging. For PET imaging, linear attenuation coefficient images are used in reconstruction to account for attenuation caused by tissue or other materials. MR scans may be used to determine the linear attenuation coefficient distribution within the MR field of view. For regions outside the MR field of view, such as the arms of a patient, or for regions in which the MR image does not accurately represent attenuating tissues or materials within the PET FOV, supplemental transmission information is used to improve attenuation correction for PET.

The supplemental transmission measurements use the magnetic field from the MR. Positrons from a source outside the PET field of view are directed as a beam by the magnetic field to one or more targets. The positrons are annihilated by interaction with electrons in the targets, creating pairs of 511 keV gamma rays that are measured by the PET detection system. The detected information is used to determine attenuation or other characteristics for the regions outside the MR field of view or elsewhere, where the MR-based attenuation information is inadequate.

Figure 1:
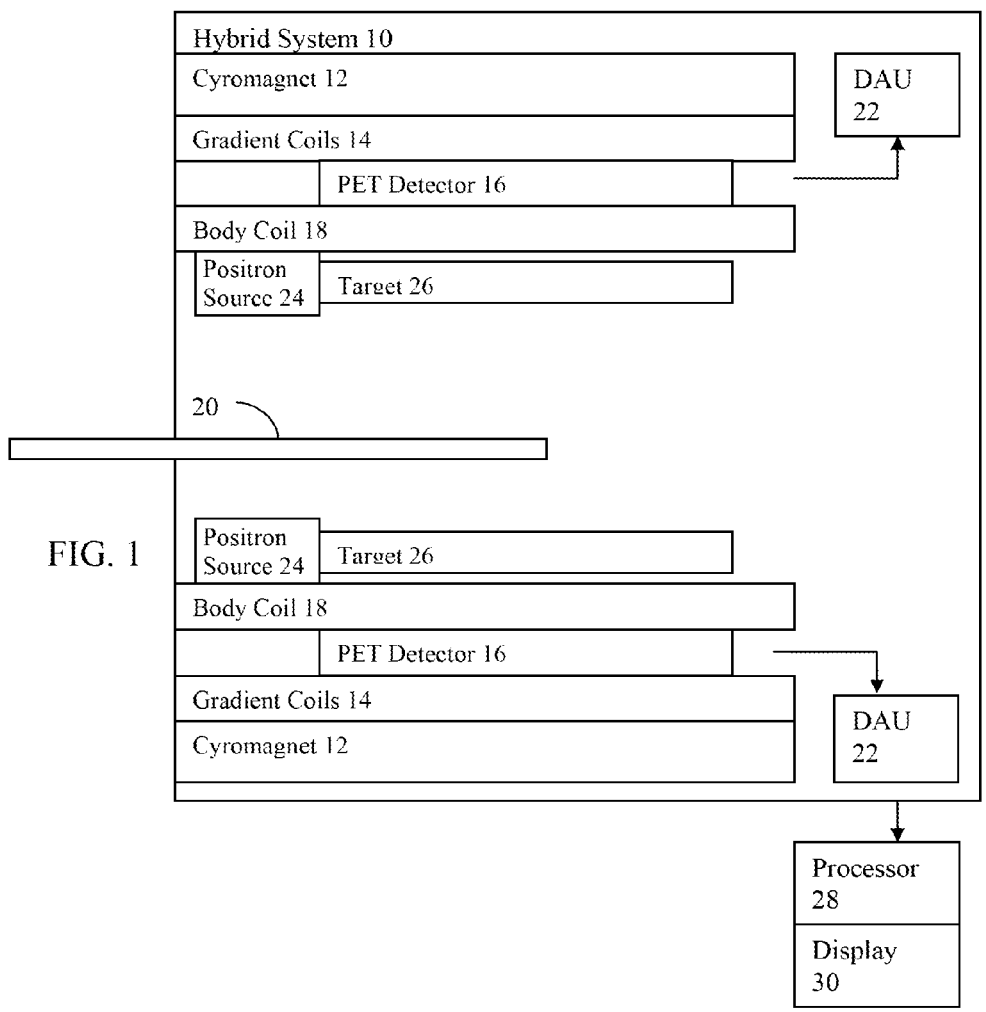
FIG. 1 is a block diagram of one embodiment of a hybrid PET/MR system.

FIG. 1 shows a hybrid magnetic resonance (MR) and positron emission tomography (PET) system 10. The hybrid PET/MR system 10 shown includes PET and MR portions. Only parts of the PET portion and only parts of the MR portion are shown. Additional, different, or fewer components may be provided.

The PET and MR portions shown are integrated into one device or within a common housing. The parts of the hybrid system 10 shown in FIG. 1 are in a single freestanding unit. In other embodiments, the components of the hybrid PET/MR system 10 shown in FIG. 1 are in separate housings or separate freestanding units. For example, the DAU 22 or parts of the DAU 22 are positioned in a separate housing within the radio frequency cabin of the MR system but separate from the MR components, such as on a filter plate for routing communications and power through the RF cabin.

The PET portion is shown as the PET detectors 16, the data acquisition unit (DAU) 22 and the processor 28. Additional, different, or fewer components may be provided. Other parts of the PET portion may include power supplies, communications systems, image processing systems, tomographic reconstruction systems, and user interface systems. Any now known or later developed PET imaging system may be used with the modifications discussed herein. The location of the different components of the PET portion may be within or outside the RF cabin. For example, the image processing, tomography, power generation, and user interface components are typically placed outside the RF cabin. Power cables and fiber optic cables for communications connect the DAU 22 with the processor 28 and other components outside the RF cabin through a filter plate.

The processor 28, memory, and/or a display 30 are part of the hybrid system 10 or are separate (e.g., a computer or workstation). The processor 28 and display 30 may be specific to the MR or PET portions or may be shared by both portions.

The MR portion is shown as the cyromagnet 12, gradient coils 14, body coil 18, and patient bed 20. Additional, different, or fewer components may be provided. Other parts of the MR portion are provided within a same housing, within a same room (e.g., within the radio frequency cabin), or within a same facility. The other parts of the MR portion may include local coils, cooling systems, pulse generation systems, image processing systems, and user interface systems. Any now known or later developed MR imaging system may be used with the modifications discussed herein. The location of the different components of the MR portion is within or outside the RF cabin, such as the image processing, tomography, power generation, and user interface components being outside the RF cabin. Power cables, cooling lines, and communication cables connect the pulse generation, magnet control, and detection systems within the RF cabin with the components outside the RF cabin through a filter plate.

The cyromagnet 12, gradient coils 14, and body coil 18 are in the RF cabin, such as a room isolated by a Faraday cage. The MR portion is configured to have a tubular or laterally open examination subject bore 32 enclosing a MR field of view. The bore 32 corresponds to the inner surface of the radio frequency body coil 18, and is a cylinder with a long axis and radius. Other bore arrangements may be used.

The patient bed 20 (e.g., a patient gurney or table) supports an examination subject such as, for example, a patient with a local coil arrangement. The patient bed 20 may be moved into the examination subject bore 32 in order to generate images of the patient. In one embodiment, a local coil arrangement for acquiring images of a local region (e.g., the head) may be placed on or adjacent to the patient. Received signals may be transmitted by the local coil arrangement via, for example, coaxial cable or radio link (e.g., via antennas) for image generation.

In order to examine the patient using the MR portion, different magnetic fields are temporally and spatially coordinated with one another for application to the patient. The cyromagnet 12 is a MR magnet for generating a strong static main magnetic field $B_0$ in the range of, for example, 0.2 Tesla to 3 Tesla or more. The main magnetic field $B_0$ extends throughout the RF cabin along magnetic field lines. Different regions within the RF cabin may be subjected to stronger or weaker magnetic fields. However, the main magnetic field $B_0$ is approximately homogeneous within a portion of the examination subject bore 32. A radius within the bore 32 but less than the radius of the bore 32 may define the extent of the undistorted MR field of view (e.g., a 60 cm bore 32 with a 45 cm MR field of view radius). At larger radii, inhomogeneities in the main magnetic field $B_0$ as well as non-linearities in the gradient magnetic fields generated by the gradient coils 14 and used for spatially encoding the MR signal, may cause distortion of the MR image.

The nuclear spins of atomic nuclei of the patient are excited via magnetic radio-frequency excitation pulses that are transmitted via a radio-frequency antenna, shown in FIG. 1 in simplified form as a body coil 18, and/or possibly a local coil arrangement. Radio-frequency excitation pulses are generated, for example, by a pulse generation unit controlled by a pulse sequence control unit. After being amplified using a radio-frequency amplifier, the radio-frequency excitation pulses are routed to the body coil 18 and/or local coils.

The gradient coils 14 radiate magnetic gradient fields in the course of a measurement in order to produce selective layer excitation and for spatial encoding of the measurement signal. The gradient coils 14 are controlled by a gradient coil control unit that, like the pulse generation unit, is connected to the pulse sequence control unit.

The signals emitted by the excited nuclear spins are received by the body coil 18 and/or at least one local coil arrangement. The body coil 18 and/or local coils are MR detectors used for generating an MR image. The body coil 18 is a single-part or includes multiple coils. The signals are at a given frequency band. For example, the MR frequency for a 3 Tesla system is about 128 MHz+/−500 KHz. Different center frequencies and/or bandwidths may be used. For a coil that may be operated both in transmit and in receive mode, such as the body coil 18 and/or the local coil, correct signal forwarding is controlled using an upstream-connected duplexer.

In some MR tomography procedures, images having a high signal-to-noise ratio (SNR) may be recorded using local coil arrangements (e.g., loops, local coils). The local coil arrangements (e.g., antenna systems) are disposed in the immediate vicinity of the examination subject on (anterior), under (posterior), or in the patient. The received signals are amplified by associated radio-frequency preamplifiers, transmitted in analog or digitized form, and processed further and digitized by a receiving unit. The recorded measured data is stored in digitized form as complex numeric values in a k-space matrix. An associated MR image of the examination subject may be reconstructed using a multidimensional Fourier transform from the k-space matrix populated with values.

From the measured MR data, the linear attenuation coefficient distribution or other characteristic of the patient may be determined. For example, the type of tissue within the MR field of view is determined using segmentation of the MR image, image processing techniques, or tissue-specific imaging. The known 511 keV gamma-ray attenuations of the tissues are used to assign attenuation coefficients for different locations. Other processes for MR-based attenuation correction in PET imaging may be used, such as atlas-based approaches. In one such atlas-based approach, a database, or atlas, of correlated CT and MR images is constructed. Each new measured MR image is spatially registered to the MR images in the atlas, and the corresponding CT image extracted. The Hounsfield units of the CT image are then appropriately scaled to linear attenuation coefficients at 511 keV. This approach may not account for abnormal anatomy due to disease or injury.

An image processing unit may generate an image from the measured MR data. The image is displayed to a user via an operator console and/or stored in a memory unit. A central computer unit controls the individual system components.

The PET detectors 16 are crystals or other photon detectors. For example, the detectors 16 are scintillation crystals coupled to avalanche photo diodes. In other embodiments, scintillation crystals are coupled with photomultiplier tubes. The scintillation crystals are bismuth germanium oxide, gadolinium oxyorthosilicate, or lutetium oxyorthosilicate crystals, but other crystals may be used.

The detectors 16 are arranged individually or in groups (e.g., cassettes). The detectors generate three analog signals, two position signals and one energy signal. Each of the signals is output as a differential signal pair. The PET detectors 16 are positioned axially within the bore of the MR portion, and radially between the gradient and RF body coils, within the main magnetic field.

Interference in the signal chain may be introduced by this positioning. The PET detectors 16 are within the magnetic field generated by the cyromagnet 12. Being within the core of the cyromagnet 12, the PET detectors 16 are subjected to similar $B_0$ magnetic field strength as the patient.

Coaxial, twisted pair, or other cables provide the signals from the PET detectors 16 to the DAU 22. Multiple DAUs 22 are provided, such as one for each pair of cassettes of PET detectors 16. Each PET signal is to be quantized and time stamped by the PET DAU 22. Since the DAU 22 is located within the RF cabin (e.g., in the same housing or shroud as the coils 14, 18 or on the filter plate), noise from the PET DAU 22 should be reduced to a minimum. Achieving high levels of bi-directional attenuation at the MR frequency, for both differential and common signals, prevents interference with the MR imaging.

The MR portion may be used to provide information for PET imaging. Since the field of view for the MR portion may be limited by the location of uniformity of the main and gradient magnetic fields, accurate information is not provided for some locations imaged in PET. Supplemental PET transmission measurements are used to acquire data for locations outside the undistorted MR field of view. Supplemental PET transmission may also be acquired for locations within the undistorted MR field of view, such as acquiring the supplemental PET transmission information to distinguish between tissues not separated by the MR image or to account for disease or abnormalities not distinguished in an atlas-based approach. The supplemental information may be used to deal with any source of inaccuracy in attenuation estimation.

For the supplemental transmission data acquisition, one or more positron sources 24 are provided. The positron source 24 is any radioactive material for generating positrons. Material of any radioisotope may be used to generate the positron beams. In one embodiment, the radioactive material has a relatively high $\beta^+$-decay branching fraction and high end-point energy to reduce extraneous radiation and minimize attenuation in air. For example, a pill of $^{68}$Ge/$^{68}$Ga is used. In other examples, $^{22}$Na or $^{18}$F is used.

Since only the attenuation of portions of the body such as the arms or other spatially limited locations are to be measured, not the entire body, the intensity may be lower than for measuring in the entire bore 32. For example, target line source intensities of 50 kBq/cm may be achieved even with radioactive material containing only 1.15 MBq of $^{68}$Ge. Other amounts of the material may be provided. Using a lower activity source may avoid count rate loss due to dead time in any adjacent PET detectors 16.

The positron-producing radioactivity is contained in a compact pill. The pill has any shape and dimensions, such as a sphere, oblong shape, or cylinder. For example, the pill is about 5 mm in diameter and about 10 mm long. The size and shape may be selected to allow for extending out of shielding and placement within shielding.

FIG. 1 shows two sources 24. FIGS. 2A and 2B each show one source 24. The source 24 is positioned within the magnetic field in or near the bore 32. The position may be in a housing of the bore 32, on the housing within or without the bore 32, or spaced from the housing within or without the bore 32.

The source 24 is positioned along the axial or long axis of the bore 32 outside the PET field of view. The ring of PET detectors 16 (e.g., ring of cassettes) defines a PET field of view. Any axial locations beyond the ring are outside the PET field of view since annihilation is detected with two events along a line of response. The source 24 is adjacent to the detectors 16 or may be spaced from the detectors 16 along the axial direction. For example, the source 24 is ten or more centimeters from the PET field of view and/or outer edges of the PET detectors 16 along the surface of the bore 32.

In one embodiment, a plurality of sources 24 is positioned within the magnetic field and outside the PET field of view. FIG. 3 shows an example. The sources 24 are distributed throughout the circumference of the bore 32. Any number and corresponding spacing may be used. The spacing is even or irregular. Sources 24 are positioned only on one side or end of the PET field of view or on both sides or ends. The sources 24 may be positioned near the inner surface of the RF body coil 18, as shown in FIG. 3, or they may be positioned near the outer surface of the RF body coil 18, between the body coil 18 and the PET detectors 16. Other positions may be used, including within the PET FOV with a well shielded source 24.

Due to the magnetic field, positrons generated by the sources 24 follow the magnetic field lines. The magnetic field alters the omni-directional path of the positrons into a beam travelling along a line (e.g., helical path of the positrons around the line) as a consequence of the action of the Lorentz force on the transverse components of the positron's velocity. The relative position of the sources 24 to the magnetic field within the bore 32 is set so that the positron beams extend axially (e.g., along the long axis) into the bore 32 and PET field of view. Using multiple sources 24, positron beams parallel to the PET and/or MR scanner's axis are injected into the PET FOV from at least partially unshielded emission sources external to the PET FOV.

As an alternative to multiple sources 24 or to reduce the number of sources 24, a rotation mechanism may be used. The source or sources 24 are positioned on a moveable ring. By rotating the ring, the source 24 or sources 24 may be positioned at different locations around the circumference of the bore 32. The rotation allows a transmission scan similar to a conventional rod source scan.

The sources 24 are positioned adjacent to a shield. For example, the shield is formed in the housing of the bore 32. The shield is a lead or other dense material for preventing propagation of the positrons into the PET field of view. In one approach, a cup or cylinder of shielding material is provided for each source 24. Due to the magnetic field, the shielding may be a plate or other structure for preventing the beam from propagating into the PET field of view while allowing propagation in other directions. Greater shielding may be provided to prevent propagation in any direction.

Using a piston, gears, belts, springs or other arrangement, the shields and/or the sources 24 may be moved relative to each other. A non-magnetic mechanism is used to change the position of the sources 24 relative to the shields. The sources 24 may be shielded and extended out of the shielding for transmission.

One or more targets 26 are positioned to intersect each positron beam. The targets 26 provide a more dense material than air, resulting in more annihilation of positrons. The targets 26 provide a source of radiation detectable by the PET detectors 16. Any solid material may be used. For example, the targets are plastic wedges or tape.

The targets 26 have any shape. A flat, thin strip may be used. FIG. 2A shows an example. A wedge may be used. FIG. 2B shows an example. Other shapes may be used. The width (into the drawing sheet) may be of any dimension, such as a thin 1 cm strip or a wider 10 cm plate.

As shown in FIGS. 2A and 2B, the targets 26 are positioned obliquely to the positron beams. The positron beams have a thickness or volume, so an oblique position results in the annihilation occurring at different locations along the target 26. An annihilation line or area source is provided. The oblique position is along an axial dimension of the bore 32. The aspect ratio of the taper may be 30:1 or greater, so that over a 26 cm field of view, for example, a rise of only 9 mm or less is provided. Such a taper may be recessed into the surface of the bore 32, or implemented on either the interior or exterior surface of the bore 32. Greater or less tapers and/or field of view lengths may be provided, including targets that are normal to the positron beams.

The targets 26 are positioned within the PET field of view. As a result, the intersection of the positron beam with the target 26, and resulting annihilation source, is within the PET field of view. Long targets cutting the positron beam obliquely may effectively produce narrow line sources nearly parallel to the scanner's axis, and extending across the entire axial PET field of view. These annihilation line sources are used as transmission sources similar to rod sources for transmission measurements on stand-alone PET scanners. Shorter transmission line sources may be provided (i.e., less than the entire axial length of the field of view) by using targets that cut the positron beams less obliquely. Transmission sources confined to an axial point may be provided by targets that cut the positron beams normally.

FIG. 2A shows a hinged target 26. The target 26 is a narrow plastic "ruler" hinged on one end. When the source 24 is extended from or positioned outside the shielding, the target 26 is moved into the oblique position relative to the positron beam. The target 26 rises from the surface of the MR RF body coil that serves as the patient tunnel on the hybrid system (i.e., rises from the surface of the bore 32). For example, the radioactive source 24 is attached to the underside of the free end of the target 24 and retracts into a shielding capsule when the target 26 is lowered. FIG. 2B uses a target 26 with a fixed taper. The target 26 attaches to the bore 32. The source 24 and/or shield moves without moving the target 26.

In alternative embodiments, the target 26 is a double wedge with a source on each side. A peak is provided in the middle of the field of view. Using a single wedge, a radioactive source 24 may be used at each end of the taper (i.e., one above and one below the strip of target 26 in FIG. 2A) to double the line source strength. Other arrangements of the target 26 relative to the source 24 may be used.

Referring to FIG. 3, each source 24 corresponds to the circumference position of a line source extending into and/or out of the drawing. Each line source enables the measurement of a fan of lines of response (LORs) across the PET field of view. Any line of response passing through the line source and intersecting the PET detectors 16 at both ends may be used. The PET detector ring is exterior to the body coil and not shown in FIG. 3. The LORs intersecting the arm 36 of the patient 34 are of interest, so example LORs associated with some of the line sources are shown as LORs a and b. The LORs labeled "a" pass through the arm and are useful for determining the attenuation and/or size of the arm. The LORs labeled "b" just graze the body and are thus useful for estimating the boundary of the arm.

The processor 28 is a general processor, digital signal processor, graphics processing unit, application specific integrated circuit, field programmable gate array, digital circuit, analog circuit, combinations thereof, or other now known or later developed device for processing detected line-of-response events, sinogram, and/or listmode data. The processor 28 is a single device, a plurality of devices, or a network. More than one device, parallel or sequential division of processing may be used. Different devices making up the processor 28 may perform different functions, such as one processor for locating arm positions and another processor for calculating attenuation. In one embodiment, the processor 28 is a control processor or other processor of the PET portion, MR potion, or hybrid PET/MR system 10. In other embodiments, the processor 28 is part of a separate workstation or computer.

The processor 28 operates pursuant to stored instructions to perform various acts described herein, such as calculating a tissue characteristic from detected radiation generated by a transmission source, determining attenuation factors, locating tissue positions, and/or reconstruction. The processor 28 is configured by software and/or hardware to perform or control performance any or all of the acts of FIG. 4.

The processor 28 is configured to calculate a linear attenuation coefficient. The attenuation coefficient along each line of response or group of lines of response through the arms or other specific locations is determined. The detected radiation along the lines of response is used to measure the attenuation. The positron beam intersecting the target is used to determine attenuation.

In one embodiment, the processor 28 is configured to calculate the linear attenuation coefficient by subtracting emission data without the positron beams intersecting the targets from emission data with the positron beams intersecting the targets, both while a patient is within the bore 32. Measurements are performed with the source 24 shielded and with the source unshielded. The differences distinguish emission from the annihilation line sources from background, patient, or other sources.

The processor 28 may be configured to perform one or more corrections of the linear attenuation coefficients. For example, the processor 28 normalizes the linear attenuation coefficient data. The results of the subtraction are normalized by results from a calibration or other blank transmission scan. Without a patient 34 in the bore 32, emissions are measured with the sources generating positron beams (i.e., unshielded). These blank scan measurements are used to normalize the linear attenuation coefficient for a particular patient. Corrections for the attenuation of hardware components in the FOV having known location and attenuation coefficients may be made. The incomplete MR-based linear attenuation coefficient information for locations within the MR field of view, where accurate, may also be used to help determine the linear attenuation coefficient for LORs passing through the arm or other regions outside the MR field of view, or where the MR-based information is inaccurate.

The processor 28 may perform other functions. For example, the processor 28 may determine other characteristics than attenuation coefficient from the measured data. The processor 28 may perform tomography or reconstruction. The reconstruction is from emission data acquired with the sources shielded, or with them exposed, or both, but includes the linear attenuation coefficient information.

The detected events, line-of-response information (e.g., sinograms), attenuation coefficients, corrections, normalizations, reconstructed image, or other data is stored in the memory. The data is stored in any format. The memory is a buffer, cache, RAM, removable media, hard drive, magnetic, optical, database, or other now known or later developed memory. The memory is a single device or group of two or more devices. The memory is part of the PET/MR system 10 or a remote workstation or database, such as a PACS memory.

The memory is additionally or alternatively a non-transitory computer readable storage medium with processing instructions. The memory stores data representing instructions executable by the programmed processor 28 for determining linear attenuation coefficients from supplemental transmission measurements in PET. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 30 is a CRT, LCD, plasma screen, projector, printer, or other output device for showing an image. The processor 28 reconstructs the patient or object being scanned from LOR information with consideration of the attenuation along different LORs. The reconstruction is used for three-dimensional rendering, multi-planar reconstruction, or two-dimensional imaging of the function of the object or patient. The images are displayed on the display 30. The display 30 may additionally or alternatively display MR images generated by the MR portion.

Figure 4:
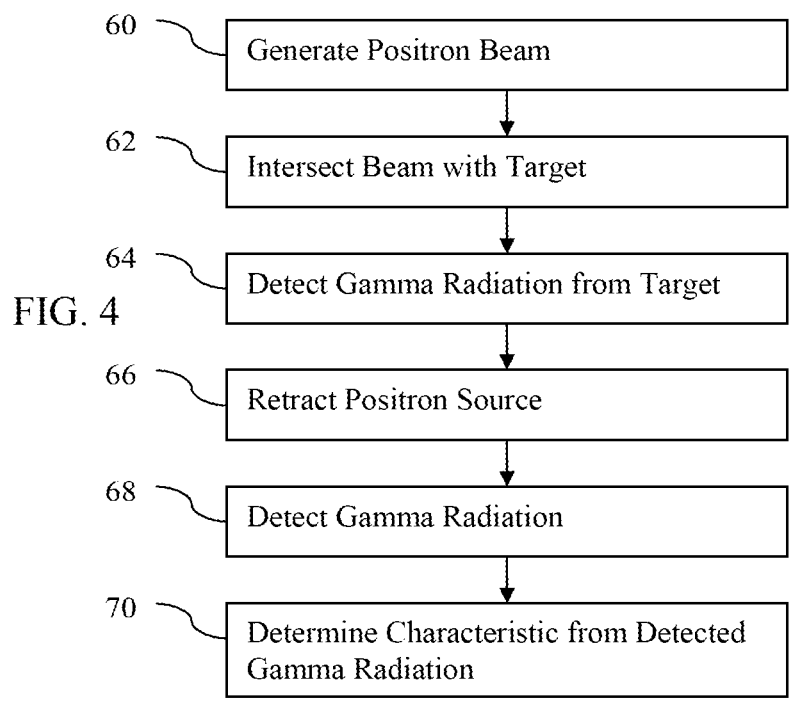
FIG. 4 is a flow chart diagram of an example embodiment of a method for determining a characteristic in a region outside an MR field of view using a positron beam formed by a magnetic field.

FIG. 4 shows a method for determining a characteristic of tissue for PET imaging in regions where the MR-derived image of PET linear attenuation coefficients may be distorted, truncated or otherwise inaccurate. The acts of FIG. 4 apply to clinical settings where a patient is being scanned by a PET system, such as PET portion of a hybrid PET/MR system. The method is implemented using the system 10 of FIG. 1 or other systems. The method is performed in the order shown, but other orders may be used. For example, acts 60, 62, and 64 are performed after acts 66 and 68 and/or are interleaved with acts 66 and 68 in a repeating pattern. Additional, different, or fewer acts may be provided, such as normalization, calibration, and/or correction.

In one embodiment, the method is for determining linear attenuation coefficients for lines of response or portions of sinograms associated with arms or other parts of a patient inadequately characterized by MR imaging, such as those outside the MR field of view. The magnetic field enables the transmission source or positron beam for determining attenuation, and the attenuation is used in PET imaging. For a PET system alone or without the magnetic field, post-injection transmission scanning is performed using radioactive rod sources in the PET field of view. For a hybrid system where a magnetic field may be generated, the correction of the emission contamination is provided in a simplified manner by positron beam sources outside of the PET field of view.

The discussion below for FIG. 4 is generally with respect to one positron source, target, and corresponding annihilation line source. In other embodiments, the acts are repeated or also performed for other sources, targets, and line sources to perform act 70.

In act 60, a positron beam is generated. A source of positrons is positioned in the bore outside a cylinder formed by PET detectors. Since the source is outside the PET field of view, the positron beam is generated outside the PET field of view.

To form the positron beam, a magnetic field is applied. The positrons emitted by the source travel along the magnetic field in a helical or other pattern, forming a positron beam directed by the magnetic field. The main magnetic field $B_0$ of the MR portion of the PET/MR hybrid system causes the positrons to travel along a particular line rather than in random directions.

Where the source or shield is moveable, the source is positioned relative to the shield to allow propagation of the positrons along the beam direction. The source is unshielded, at least with respect to β+ emissions, for generating the positron beam.

The positron beam propagates into the PET field of view where the positron beam is used to generate a transmission line source within the PET field of view. The line source provides annihilation gamma rays passing along lines of response through many regions of the patient's body including those corresponding to distorted, truncated or inaccurate regions of the MR-based image of linear attenuation coefficients.

In act 62, the positron beam is intersected with a target. A solid material, such as plastic, is positioned to be hit by the beam. The target is positioned in a way that provides the desired spatial extent of an annihilation source. For example, the target is oblique to the beam, resulting in an oblong or line annihilation source. Non-oblique intersection may be used for a point source. A plurality of point sources may be positioned to intersect a positron beam at different locations.

The target is positioned to intersect the beam within the field of view of the PET detectors, but outside the homogeneous region of the main magnetic field. The inhomogeneities of the $B_0$ field within the PET FOV are not large enough to significantly affect the positron beam. The intersection of the target with the beam may also occur within the homogeneous region of $B_0$.

The target is in a fixed position. By shielding and unshielding the positron source, the annihilation source may be turned on and off. Alternatively or additionally, the target is moveable. By moving the target relative to the positron beam, the annihilation source may be turned on or off and/or shifted in position.

The positrons interact with electrons in the target, generating annihilation radiation. The two rays, such as gamma rays, resulting from a given annihilation propagate generally along a line (i.e., in two directions about 180 degrees apart).

In act 64, the rays are detected with PET detectors. The detection is performed as known in the art for annihilation radiation detection. The emission data acquired in act 64 are organized into a sinogram array. Each element of a sinogram corresponds to a pair of detectors defining a line of response that detect the two gamma rays from an annihilation event in time coincidence. Alternatively, these data may be stored as a listmode file with one event word for each detected coincidence event. The source of the annihilation events of interest is from the interaction of positron beams with targets in the PET FOV rather than from decay of a positron emitting radioactive tracer within a patient. Annihilation from other sources may be detected as well.

Annihilation events are detected along lines of response for desired locations. Elements of the sinograms for lines of response possibly intersecting the arms or other regions outside the MR field of view are obtained. Where the patient holds their arms against their torso, the arms may still be outside the MR field of view. The events associated with lines of response through the arms may be used to determine attenuation.

To estimate the attenuation, the emissions from the transmission sources are compared to measurements without the transmission sources. In act 66, the positron source is retracted into a shield. The positrons are blocked from intersecting the target. Alternatively, the target is moved to avoid intersection with the positron beam. In this case, there would be a small residual annihilation of the positron beam in air, that could be compensated for in the blank scan as discussed below.

In act 68, radiation is detected while the transmission source is not generating annihilation events, or generating only annihilation in air. While the positron source is retracted or the target moved to avoid intersection, annihilation events are detected with the PET detectors. Gamma radiation due to emissions from within the patient and/or background radiation may occur along lines of response through the region of interest, including beyond the MR field of view.

To determine attenuation or other characteristic of tissue from the transmission source in act 70, the information from the transmission source is isolated from other sources. During the PET emission scan, the positron sources are extended or generate an intersected positron beam for some fraction, f, of the total scan time and retracted for the rest, giving pure emission (EM) data from other sources. A single or multiple on-off periods are used to minimize the effects of motion or emitter redistribution. That data for the different fractions and corresponding detection periods is acquired as separate frames or sorted retrospectively from listmode data based on the count rates in LORs passing through the source positions.

In act 70, the characteristic, such as attenuation, of tissue in the region outside the MR field of view or at other locations is determined. For example, the attenuation correction factor for locations associated with arms is determined.

The emissions generated by the transmission line source are used to determine the characteristic. Other emissions may be used as well, such as the emissions occurring when the transmission line source is not active. To isolate the attenuation, the differences in sinograms due to the transmission line sources are determined. For example, the attenuation correction factors are determined from the differences in gamma radiation detected in acts 64 and 68. Additionally, emissions from a calibration measurement where the transmission line source is active but no patient is present (i.e., blank scan) are used for normalization of the intensities of the transmission sources.

In one embodiment, emission-only data (EM) representing the gamma radiation detected while the positron source is retracted (i.e., is shielded or not active) is subtracted from transmission plus emission data (TX) representing the gamma radiation detected while the target intersects the positron beam. The fraction of time associated with the scans weights the function. For example, the emission-corrected TX scan, TX', is represented as TX'=TX−EM(f/(1−f)), where f is the fraction of the combined data acquisition time during which the TX data are measured. Alternative weighting schemes may be used. The TX' data represent the equivalent of a transmission-only scan for estimating the PET linear attenuation coefficients.

The emission data from the EM and TX scans are combined and reconstructed to form the PET emission image. The emission image is a representation of the distribution of positron-emitting radioactive tracers present in the body of the patient being scanned. To produce a quantitatively accurate image, the emission sinogram data is corrected by an ACF sinogram during reconstruction to compensate for the attenuation of the annihilation radiation along measured LORs. This emission image may show bright spots at the source locations near the edge of the PET field of view, but these bright spots are known and so may be masked out. If time of flight information with adequate resolution is available, these sources may be excluded from the image based on their time offset. In one alternative embodiment, the data for the bright spots of the targets is not removed. In another alternative embodiment, only the EM data are used to reconstruct the emission image, eliminating the bright spots, but increasing noise in the image.

The transmission data TX' are normalized with data from a blank transmission scan (BLNK), to account for the transmission source intensities. Data from a scan with the transmission line sources active (e.g., extended out of the shielding) but no patient or other removable objects in the PET field of view are used for the BLNK. In the case that the EM scan is measured by moving the target to avoid intersection with the positron beam, a second blank scan is made with the target removed from the beam, allowing only positron annihilations from the beam in air. The final BLNK scan is the difference between the first and second scans. The BLNK and TX' scans are scaled to match their acquisition times. The BLNK scan is performed prior to clinical scanning of the patient, but may be performed after the clinical scanning. In alternative embodiments, normalization is not provided.

An attenuation correction factor (ACF) sinogram is formed as: ACF=BLNK/TX'. Noise reduction, dead time correction, or other refining operations may be performed. For example, the ACF sinogram is smoothed.

The ACF is measured for each element of the sinogram that corresponds to an LOR passing through one or more of the transmission sources. In the case that only a few transmission sources in fixed positions are used, the ACF sinogram may be incomplete because the ACF has meaningful values only along the sinusoids corresponding to the transmission sources. However, since the positions of these sinusoids and LORs are known from the transmission source positions, the measured ACF information may be interpolated, extrapolated or otherwise extended to other regions of space The ACF sinogram may be partially known from other sources of information, e.g., segmented MR images of the patient, or x-ray computed tomography (CT) images of the hardware components. In this case, it is only necessary to estimate the ACF in regions where the prior information is missing or inaccurate (e.g., for LORs passing through arms that are truncated in the MR images, or bone that has been classified as lung tissue). To better focus on only these unknown or inaccurate regions, the sinogram representing the measured ACF may be adjusted for known attenuation components in the field of view. The ACF for a particular LOR represents the exponential of the line integral through the linear attenuation coefficient (LAC) distribution along that LOR. If there are multiple components in the LAC distribution, their line integrals are added and their ACFs are multiplied together to give the total ACF. For example, the hardware (e.g., bed and fixed coils) factor in the ACF, $ACF_{hdwr}$, may be computed from line integrals through their CT-based LAC images, and the human ACF ($ACF_{MR}$) factor may be computed from line integrals through the (possibly incomplete or inaccurate) MR-based human LAC image. An adjusted ACF sinogram, ACF', may then be computed as: ACF'=ACF/($ACF_{hdwr}ACF_{MR}$). The transformation is only applied to the meaningful bins along the measured sinusoids. The values in ACF' differ from 1 only in regions where the measured ACF differs from the prior assumed ACF, $ACF_{hdwr}ACF_{MR}$, and thereby indicates where and by how much this prior ACF needs correction, for example in truncated arms outside the MR FOV, or in non-fixed coils, such as the body matrix coil.

The characteristic, such as attenuation, is determined for tissue regions outside the MR field of view. The tissue regions are distinguished from locations outside the MR field of view not associated with tissue. For example, the ACF or ACF' is determined for some locations and not others outside the MR field of view.

Any technique may be used to identify the locations of interest. For example, arm or other tissue positions are identified from the ACF data. In most scanning situations in MR/PET, the arms lie along the side of the patient. A cross section through the arm in a trans-axial plane has a convex boundary. Other positions with other boundaries may be provided.

The convex hull of a portion of the arm truncated in the MR image is determined from the envelope of the values in ACF' that are >1. Air likely has an ACF' of 1 or about 1. ACF' is normalized by the blank scan, so tissue has a greater ACF'. The envelope is found as a boundary of the ACF' above a threshold. Gradient or other processing may be used to find the envelope or convex boundary. In FIG. 3, the LORs labeled "b" are tangential to this boundary or envelope.

Distinct envelopes for the left and right arms are determined. Since in lateral views in the sinogram the arms overlap in only a small region, distinct envelopes may be located. Locations within the envelope are tissue locations.

Once the locations are determined, linear attenuation coefficients may be determined. The sum of the linear attenuation coefficients along the LORs is estimated from the logarithm of the ACF' values for the LORs. Any technique may be used.

In one embodiment, a linear attenuation coefficient tissue value is assigned to the arm positions. A representative tissue value is predetermined. Any tissue locations are assigned the value. Different values may be used for different tissues, such as modeling the arm as soft tissue and bone where different attenuation values are assigned based on the model. The attenuation correction factors are then calculated as an exponential of the integral of the linear attenuation coefficient values assigned along various lines of response.

In another embodiment, the linear attenuation coefficients are reconstructed from a log of the attenuation correction factors for lines of response through an arm of a patient. The sinograms representing the ACF' are used to determine the linear attenuation coefficients (LACs). Once the boundary of the arm is known, the ln(ACF') values of the LORs passing through the arm give the integrals of the LAC along these LORs. The linear attenuation coefficients for LORs labeled "a" in FIG. 3 are determined. Although the line integrals may not be tomographically complete, there will be enough data to iteratively reconstruct at least a coarse-grained LAC image of the arm if an adequate number of sources (e.g., 3, 4, or more, such as 12) are used. The coarse-grained LAC image may include bone, soft tissue and fat, but more or less refined distinction between tissue types may be used.

The resulting LACs are used in PET reconstruction. The reconstruction accounts for attenuation. For locations or LORs passing through tissue in the MR field of view where the MR-based LAC image is accurate, the attenuation from MR measurements is used. For locations or LORs passing through tissue outside the MR field of view or where the MR-based LAC image is inaccurate, the attenuation from the transmission line sources is used. For LORs passing through tissues both within and outside of the MR field of view, or through regions where the MR-based LAC image is inaccurate and regions where the MR-base LAC image is accurate, the attenuations from both techniques are used.

The acts of FIG. 4 may be applied in experimental settings. For example, the acts are tested with a 20 cm $^{68}$Ge phantom on a phantom holder in the center of the PET field of view. A cold water bottle is placed beside the phantom and supported on foam blocks to emulate an arm. A positron beam line source is placed on the tunnel beneath the phantoms. The positron beam line source is formed by the single $^{68}$Ge pill mounted about 5 mm above a 36 cm long Plexiglas ruler raised on one end to give a 40:1 aspect ratio. The pill is entirely outside the PET field of view. Additional line sources, different amounts of source material, different sizes of the target, and different aspect ratios may be used.

In this example, two acquisitions are performed. The first acquisition is a transmission scan with the phantoms in place and the source of positrons unshielded. The second is a blank scan with the phantoms removed. Each scan is 3500 sec in duration, but other durations may be used. The blank scan has about 3.6e7 net trues, but other numbers may result.

FIGS. 5A-C and 6A-C show example resulting information from the experimental scans. FIGS. 5A and 6A are the same except for the position of the horizontal line for which the profiles in FIGS. 5C and 6C are shown, and FIGS. 5B and 6B are the same except for the position of the horizontal line for which the profiles in FIGS. 5C and 6C are shown. FIGS. 5A-C represent views in which the source is not behind the bottle or arm, and FIGS. 6A-C represent views in which the source is behind the bottle so attenuation due to the bottle occurs.

FIGS. 5A and 6A represent the transmission sinograms averaged over central planes. FIGS. 5B and 6B represent the blank sinograms averaged over the central planes. In FIGS. 5A-B and 6A-B, the sinusoid of the transmission source is shown, represented as a parabola-like curve. As shown in FIGS. 5A and 6A, the bottle causes attenuation of the sinusoid around Y=20-45. The light region from about x=125-225 is from the phantom. The darker slash or angled region in the phantom is from the bottle and extends into the attenuation along the sinusoid.

The horizontal lines in FIGS. 5A-B and 6A-B represent a view angle of about 32 degrees. In FIGS. 5A-B, the horizontal line is outside the attenuation region of the sinusoid. In FIGS. 6A-B, the horizontal line intersects the attenuation region of the sinusoid. The sinogram profiles of FIGS. 5C and 6C are along the respective horizontal lines. One profile is from the transmission scan of FIGS. 5A and 6A and the other profile is from the blank scan of FIGS. 5B and 6B. Where the profile line intersects the attenuation region of the sinusoid, the amplitude is different for the blank and transmission scans (see difference at about x=245 in FIG. 6C). Where the profile line does not intersect the attenuation region of the sinusoid, the amplitudes are the same for the sinusoid location (see no difference at about x=245 in FIG. 5C). FIG. 5C is for a view angle for which the transmission source is just outside the water bottle and thus the source is not attenuated.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for attenuation correction for positron emission tomography (PET) in a combined PET and magnetic resonance (MR) imaging system, the method comprising:
generating, with a positron source in a magnetic field, a positron beam extending into a field of view of PET detectors of the combined PET and MR system;
intersecting the positron beam with a target within the field of view of the PET detectors;
detecting, with the PET detectors, gamma radiation resulting from the intersection of the positron beam with the target;
determining attenuation correction factors as a function of the detected gamma radiation;
retracting the positron source into a shield; and
detecting, with the PET detectors, gamma radiation while the positron source is retracted into the shield;
wherein determining comprises subtracting data representing the gamma radiation detected while the positron source is retracted from data representing the gamma radiation detected while the target intersects the positron beam.

2. The method of claim 1 wherein generating comprises generating with a pill of radioactive material external or internal to the field of view of the PET detectors and within a bore of the combined PET and MR imaging system, the pill being at least partially unshielded against β+ emission.

3. The method of claim 1 wherein generating comprises directing positrons from the positron source with a main magnetic field of an MR portion of the combined PET and MR imaging system.

4. The method of claim 1 wherein intersecting comprises positioning a solid material as the target to intersect the positron beam obliquely within the field of view.

5. The method of claim 1 wherein the generating, intersecting, and detecting are performed for each of a plurality of positron sources and targets.

6. The method of claim 1 wherein detecting comprises detecting for locations associated with arm positions against a torso.

7. The method of claim 1 wherein determining comprises normalizing the attenuation correction factors with data from a blank transmission scan.

8. The method of claim 1 wherein determining comprises correcting for a attenuation component in the field of view.

9. The method of claim 1 further comprising:
locating arm positions from the attenuation correction factors.

10. The method of claim 9 further comprising:
assigning a linear attenuation tissue value to the arm positions.

11. The method of claim 1 further comprising:
reconstructing linear attenuation components from a log of the attenuation correction factors for lines of response through an arm of a patient.

12. A hybrid magnetic resonance (MR) and positron emission tomography (PET) system comprising:
a MR magnet for generating a magnetic field in a bore;
PET detectors within the magnetic field;
a plurality of positron sources spaced apart within the magnetic field, wherein the positron sources are positioned outside a field of view of the PET detectors;
a shield inside the bore;
a non-magnetic mechanism configured to change positions of the positron source relative to the shield, wherein the positron sources are movable between a shielded position in which positron beams are not generated and an unshielded position in which positron beams are generated; and
the positron beams generated by the positron sources in the magnetic field in the unshielded position is configured to be positioned obliquely to a plurality of targets.

13. The system of claim 12 wherein the plurality of positron sources comprise pills of radioactive material spaced around the bore on first and second ends of the field of view and relative to the magnetic field such that the positron beams extend axially to or through the bore, and wherein the plurality of targets comprise solid material extending axially in the bore.

14. The system of claim 12 further comprising:
MR detectors for generating an MR image, and
a display for displaying MR and PET images from the system.

15. The system of claim 12 further comprising:
a processor configured to calculate a linear attenuation coefficient as a function of radiation from interaction of the positron beams with the targets.

16. The system of claim 15 wherein the processor is configured to calculate the linear attenuation coefficient by subtracting emission data without the positron beams intersecting the targets from emission data with the positron beams intersecting the targets, both while a patient is within the bore, to normalize results of the subtracting by data for a blank transmission scan, and to reconstruct the linear attenuation coefficient from the normalized results.

17. A method for determining a characteristic of tissue for positron emission tomography (PET) in a region within the PET field of view of a magnetic field where an MR image is distorted, truncated, or otherwise inaccurately represents attenuating tissues, the method comprising:

generating a positron beam by a positron source, wherein the positron source is outside a cylinder of PET detectors and is inside the magnetic field, the positron source movable between a shielded position in which the positron beam is not generated and an unshielded position in which the positron beam is generated;

producing a transmission line source within the region with the positron beam guided by the magnetic field; and determining the characteristic of the tissue in the region as a function of emissions generated by the transmission line source, wherein determining the characteristic of the tissue comprises determining an attenuation correction factor for a location within the region.

\* \* \* \* \*